United States Patent [19]

Unalmiser et al.

[11] Patent Number: 5,442,950

[45] Date of Patent: Aug. 22, 1995

[54] METHOD AND APPARATUS FOR DETERMINING PROPERTIES OF RESERVOIR ROCK

[75] Inventors: Servet Unalmiser; Terry J. Swalwell, both of Dhahran, Saudi Arabia

[73] Assignee: Saudi Arabian Oil Company, Dhahran, Saudi Arabia

[21] Appl. No.: 138,699

[22] Filed: Oct. 18, 1993

[51] Int. Cl.⁶ .................. G01N 15/08; E21B 49/00

[52] U.S. Cl. ............................................ 73/38; 73/155

[58] Field of Search .................... 73/38, 155, 153

[56] References Cited

U.S. PATENT DOCUMENTS

| | | | |
|---|---|---|---|
| Re. 32,964 | 6/1989 | Jones | 73/38 |
| 2,713,789 | 7/1955 | Kelton | 73/38 |
| 2,724,963 | 11/1955 | Ten Brink | 73/38 |
| 2,794,338 | 6/1957 | Murphy et al. | 73/38 |
| 3,030,801 | 4/1962 | Allen | 73/38 |
| 3,309,912 | 3/1967 | Boland et al. | 73/38 |
| 3,501,944 | 3/1970 | Winslow | 73/38 |
| 3,524,341 | 8/1970 | Roy | 73/38 |
| 3,683,674 | 8/1972 | Roy | 73/38 |
| 3,839,899 | 10/1974 | McMillen | 73/38 |
| 3,911,256 | 10/1975 | Jones | 235/151.3 |
| 4,170,129 | 10/1979 | Lowell | 73/38 |
| 4,203,317 | 5/1980 | Gupta | 73/38 |
| 4,272,983 | 6/1981 | Sisti et al. | 73/38 |
| 4,300,386 | 11/1981 | Gupta | 73/38 |
| 4,537,063 | 8/1985 | Barnaby | 73/38 |
| 4,552,011 | 11/1985 | Wiley | 73/4 |
| 4,555,934 | 12/1985 | Freeman et al. | 73/38 |
| 4,562,726 | 1/1986 | Barnaby | 73/38 |
| 4,608,859 | 9/1986 | Rockley | 73/153 |
| 4,627,270 | 12/1986 | Jones | 73/38 |
| 4,644,779 | 2/1987 | Sisti et al. | 73/38 |
| 4,648,261 | 3/1987 | Thompson et al | 73/38 |
| 4,649,737 | 3/1987 | Jones | 73/38 |
| 4,660,412 | 4/1987 | Gupta | 73/38 |
| 4,669,299 | 6/1987 | Closmann | 73/38 |
| 4,679,421 | 7/1987 | Barree | 73/38 |
| 4,688,238 | 8/1987 | Sprunt et al. | 378/4 |
| 4,710,948 | 12/1987 | Withjack | 378/208 |
| 4,715,212 | 12/1987 | Johanson | 73/38 |
| 4,718,270 | 1/1988 | Storr | 73/38 |
| 4,753,107 | 6/1988 | Reed et al. | 73/38 |
| 4,765,182 | 8/1988 | Boone | 73/153 |
| 4,773,254 | 9/1988 | Shen | 73/38 |
| 4,779,200 | 10/1988 | Bradbury et al. | 364/422 |
| 4,782,501 | 11/1988 | Dixon, Jr. | 378/4 |
| 4,799,382 | 1/1989 | Sprunt et al. | 73/153 |
| 4,815,316 | 3/1989 | Tantram | 73/38 |
| 4,817,423 | 4/1989 | Christiansen | 73/153 |
| 4,827,761 | 5/1989 | Vinegar et al. | 73/38 |
| 4,833,914 | 5/1989 | Rasmus | 73/152 |
| 4,854,157 | 8/1989 | Wilson | 73/38 |
| 4,907,448 | 3/1990 | Givens | 73/153 |
| 4,949,575 | 8/1990 | Rasmus | 73/152 |
| 4,961,343 | 10/1990 | Boone | 73/152 |
| 4,981,037 | 1/1991 | Holbrook et al. | 73/152 |
| 5,133,207 | 7/1992 | Wilson et al. | 73/38 |
| 5,144,589 | 9/1992 | Hardage | 367/25 |
| 5,159,828 | 11/1992 | Steiger et al. | 73/38 |
| 5,272,629 | 12/1993 | Hall, Jr. | 73/155 |

OTHER PUBLICATIONS

American Petroleum Institute, "API Recommended Practice for Core-Analysis Procedure API RP 40," (1960).

Amyx et al., "Petroleum Reservoir Engineering: Physical Properties," Reissue Edition, (McGraw Hill 1988), at 35–64.

*Primary Examiner*—Hezron E. Williams
*Assistant Examiner*—J. David Wiggins
*Attorney, Agent, or Firm*—Davis Hoxie Faithfull & Hapgood

[57] ABSTRACT

Methods and apparatus are provided for determining the pore volume compressibility, the porosity at stress and the relative porosity change of reservoir rock samples. In accordance with the invention, as few as two pore volume measurements of reservoir rock samples are obtained at simulated overburden pressures and relatively low pore pressure. From these data, a bi-logarithmic plot of pore volume versus pressure for a given reservoir rock sample is prepared. From the slope of the plot, pore volume compressibility of the reservoir rock sample at a given overburden pressure is directly calculated. In a further aspect, the intercept of the pore volume versus pressure plot is obtained, and, in conjunction with a measurement of the grain volume of the sample, the porosity at stress and relative porosity change of the rock sample are determined.

34 Claims, 3 Drawing Sheets

METHOD AND APPARATUS FOR DETERMINING PROPERTIES OF RESERVOIR ROCK

BACKGROUND OF THE INVENTION

1. Field of the Invention

This invention relates to the field of oil and gas production from subterranean reservoirs. More particularly, the invention is an improved method and apparatus for the determination of certain important properties of reservoir rock, including pore volume compressibility, porosity at stress and relative porosity change.

In the recovery of oil and gas from underground rock formations, certain characteristics and properties of reservoir rock are of importance in estimating the production potential of the reservoir. A characteristic of particular importance is pore volume, which is the aggregate void space within the rock. A related property is porosity, which is the ratio of the total pore volume to the bulk volume of such rock. The bulk volume is the sum of the total pore volume and the grain volume. Grain volume is the volume of discrete rock particles (grains), i.e., the volume of "solid" rock. Porosity is indicative of the oil and gas storage capacity within reservoir rock.

As oil and gas are withdrawn from an underground rock formation, the fluid pressure in the pores of the rock decreases. However, the external pressure on the reservoir rock, which is due, in part, to the weight of the overlying strata, remains constant. As the disparity between the external and internal pressure (the net overburden pressure) increases, pore compression occurs. As such, the porosity of reservoir rock—and therefore the oil and gas reserves of a reservoir—will vary with the net confining pressure. Pore volume compressibility is thus a measure of the production potential of a reservoir, and can also be used as to calculate hydrocarbon storage capacity of the reservoir at various production phases.

2. Description of Related Art

A number of techniques exist for measurement of the aforementioned characteristics. The standard reference for reservoir rock core analysis is API RECOMMENDED PRACTICE FOR CORE-ANALYSIS PROCEDURE by the American Petroleum Institute, API RP 40, 1960. PETROLEUM RESERVOIR ENGINEERING: PHYSICAL PROPERTIES by Amyx et al., Reissue Edition, at 36–64 (McGraw-Hill 1988) provides a discussion of reservoir rock characteristics and a useful comparison of measurement techniques.

A fluid expulsion procedure known as "liquid squeeze out" is currently the most commonly applied technique in the oil industry to measure pore volume compressibility. In this method, a core sample is saturated with either brine or oil, placed in a rubber sleeved core holder, and subjected to a simulated overburden pressure and a pore pressure. The net overburden pressure is increased stepwise by an increase in sleeve pressure or a decrease in pore pressure. Fluid, i.e., brine, is expelled from the pores as the net overburden pressure increases. The volume of expelled fluid is an indication of the pore volume reduction. Pore volume compressibility can then be calculated at any pressure according to the relation:

$$C_p = -\frac{1}{V_p} \cdot \frac{dV_p}{dP} \quad [1]$$

Where:
$C_p$ = Pore volume compressibility, vol/vol/psi
$V_p$ = Pore volume, cc
$P$ = Net overburden pressure, psi Successive readings must be taken to define the compressibility curve for a given specimen of rock taken by core sampling.

Another method for determining pore volume compressibility is described in U.S. Pat. No. 4,782,501. This method employs computed tomographic (CT) scanning based on X-ray attenuation measurements at various confining stresses.

Both methods suffer from the drawback that a number of successive measurements must be taken to define the compressibility curve for a given reservoir rock sample. Further, to the extent that a noncompressible fluid, such as brine, is used to saturate the core sample, the compressibility determined in the laboratory will be the result of a hydrostatic load which differs from the actual reservoir loading. Under actual conditions in the hydrocarbon rock reservoir, the contraction is only in the vertical direction which is referred to as unilateral or uniaxial stress. Therefore, the laboratory measured hydrostatic strain condition must be converted to the uniaxial strain condition.

Thus, there is a need for a more efficient and cost effective method and apparatus to calculate pore volume compressibility.

SUMMARY OF THE INVENTION

The present invention is a method and apparatus for determining the pore volume compressibility, the porosity at stress and the relative porosity change of reservoir rock samples. The invention applies a new model for determining pore volume compressibility as a function of pressure. This model simplifies the determination of the pore volume compressibility of a sample, since measurement of pore volume at only two pressures is required. The new model results from the technique applicants use to obtain pore volume measurements at stress (pressure).

In accordance with the present invention, pore volume measurements of reservoir rock samples are taken at least two simulated overburden pressures. Pore pressure is kept constant at near atmospheric pressure as the overburden pressure is increased. Pore pressure measurements are carried out with a known volume of an inert gas, such as helium, at low pressure. These data are used to develop a bi-logarithmic plot of pore volume versus pressure for a given reservoir rock sample. The slope of the plot is determined. These data are then used to calculate pore volume compressibility of the reservoir rock sample at a given overburden pressure via a direct and easily determined expression.

In a further aspect, the intercept of the pore volume versus pressure plot is determined, and, in conjunction with a measurement of the grain volume of the sample, the porosity at stress and relative porosity change of the rock sample can be determined.

DETAILED DESCRIPTION OF THE PREFERRED EMBODIMENT

Figure 1:
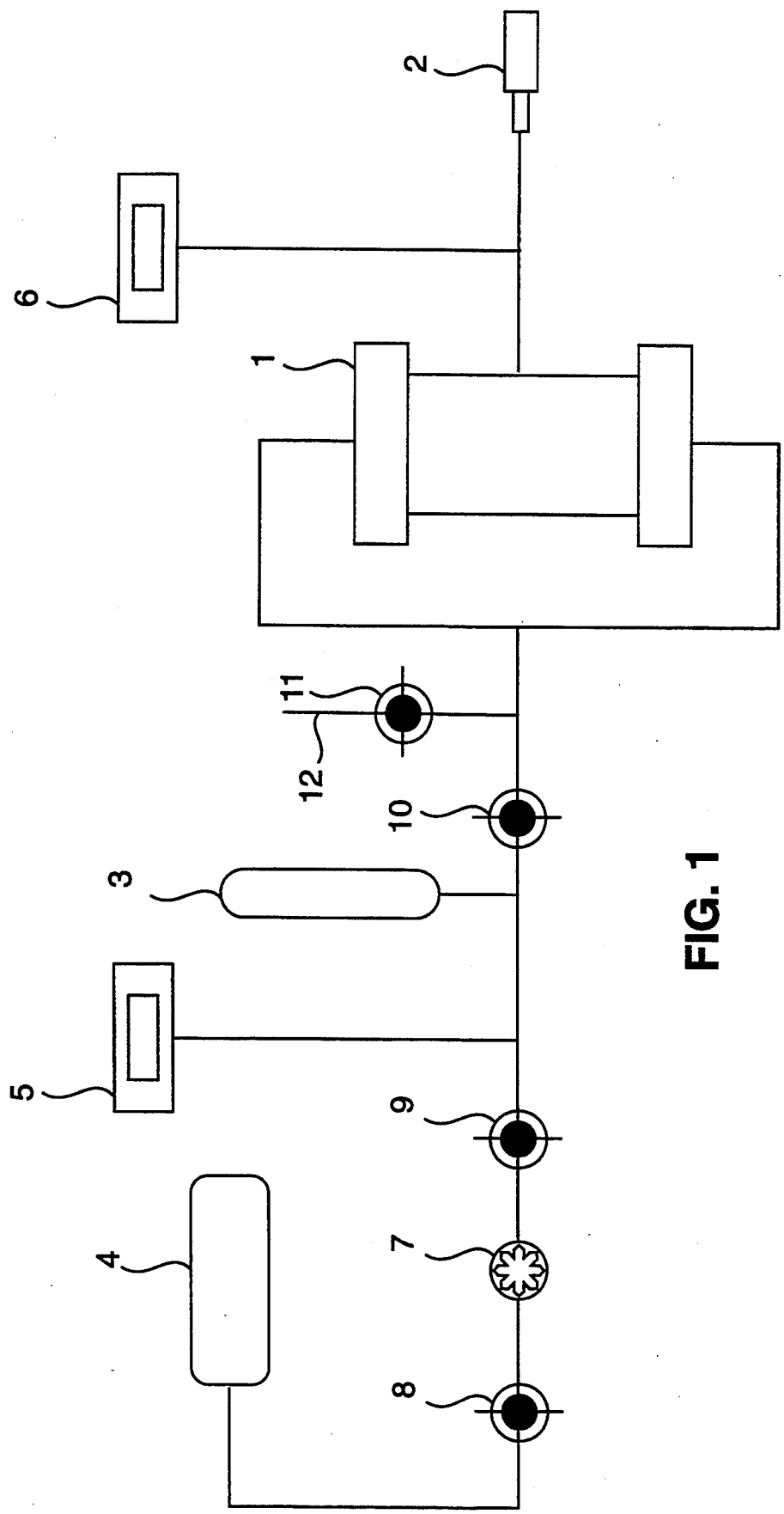
FIG. 1 is a schematic diagram illustrating one embodiment of a typical arrangement of apparatus suitable for practicing the invention.

In accordance with the invention, pore volume of a reservoir rock sample is measured with the pore pressure constant and at low pressure. The porous sample is exposed to a compressible fluid, such as helium, which is used purely as a means to measure the pore volume. This fluid is not an active part of the pressure system, i.e., does not transmit stress throughout the sample, as in conventional pore volume compressibility measurement techniques which typically saturate the pores with brine or oil. An external pressure is also imposed upon the sample, to simulate the overburden pressure to which the sample is exposed under actual conditions in a hydrocarbon rock reservoir. While the pore pressure is kept constant, the external pressure on the rock sample is increased. This results in a comparable stress on the rock matrix causing an equivalent reduction in pore volume. However, since there is no liquid present in the pore space there is no hydrostatic compression of the rock matrix, only that due to the hydrostatic stress transmitted through the matrix itself.

When pore volume is measured in this manner, an exponential relationship exists between the measured pore volume of the rock sample and the corresponding sleeve pressure:

$$V_p = b \cdot P^{-m} \quad [2]$$

Wherein:
b = intercept of log $V_p$ vs. log P, cc
m = slope of log $V_p$ vs. log P, cc/psi Taking the derivative of equation [2] with respect to pressure and substituting into equation [1] yields the following direct and easily determined relationship between the compressibility of a rock sample and net overburden pressure to which it is subjected:

$$C_p = -\frac{m}{P} \quad [3]$$

Where:
C = pore volume compressibility, vol/vol/psi

Porosity at stress (under pressure) and relative porosity change of reservoir rock can be readily calculated at the corresponding net overburden pressures. As discussed previously, porosity is defined as the ratio of pore volume to bulk volume of reservoir rock. Thus:

$$\phi_s = \frac{V_{ps}}{V_{bs}} \quad [4]$$

Where:
$\phi_s$ = porosity at stress
$V_{ps}$ = pore volume at stress, cc
$V_{bs}$ = bulk volume at stress, cc By expressing stress pore volume in terms of equation [2], and expressing bulk volume of the rock sample as the sum of grain and pore volume:

$$\phi_s = \frac{b \cdot P_s^{-m}}{b \cdot P_s^{-m} + V_g} \quad [5]$$

Where:
$V_g$ = grain volume

By definition, the relative porosity change of the reservoir rock sample is:

$$\frac{\Delta \phi}{\phi_i} = \frac{(\phi_i - \phi_s)}{\phi_i} \quad [6]$$

Where:
$\Delta \phi$ = porosity change
$\phi_i$ = initial porosity

By expressing stress and initial porosity in terms of equation [4] and in terms of initial pore and grain volume:

$$\frac{\Delta \phi}{\phi_i} = 1 - \frac{b \cdot P_s^{-m}}{b \cdot P_s^{-m} + V_g} \cdot \frac{V_g + V_p}{V_{pi}} \quad [7]$$

Where:
$V_{pi}$ = initial pore volume

Thus, pore volume compressibility, porosity at stress and relative porosity change of a reservoir rock sample are a function of readily determined parameters.

The first step of the new method is to obtain and prepare reservoir rock samples, as for example, core samples obtained by drilling at various locations and depths in the reservoir rock. Next, the prepared sample is placed in an appropriate test apparatus. A Boyle's Law porosimeter or other suitable apparatus may be used for this purpose. Preferably, a microcomputer controlled helium injection-Boyle's Law porosimeter is used. To obtain a measurement of grain volume, a helium injection-Boyle's Law technique or other suitable method can be used. Four example, see API RP 40.

A typical arrangement suitable for practicing the invention is shown in the embodiment of FIG. 1. A reservoir rock sample is placed in a Hassler type core holder 1, or equivalent. Using pump 2, frame stress (external pressure) on the sample is increased to a first selected pressure, preferably about 1500 psi. Frame stress is monitored via pressure gauge 6. During this operation, valve 10 is kept closed to isolate the reservoir rock sample from the helium system, which is comprised of helium supply 4, cell 3, pressure gauge 5, regulator 7 and valves 8-10. Valve 11 is in the open position so that pore pressure is maintained at atmospheric pressure.

After the desired frame stress is obtained, pore volume measurements are taken as described below. With valve 10 closed, and valves 8 and 9 open, helium is introduced to the system. Helium pressure is increased to pressure $P_1$, e.g., about 100 psig, by regulator 7, and then valve 9 is closed. The volume, $V_1$, between valves 9 and 10, which consists of cell 3 volume and the line volume, is known from prior determinations. Valve 11 is then closed, and valve 10 is opened, allowing trapped helium in the volume $V_1$ to fill the pore volume $V_p$ of the rock sample, as well as the known line volume $V_2$ between valve 10 and the rock sample. The equilibrium pressure $P_2$ is monitored from pore pressure gauge 5.

Based on the Boyle's Law principle, the pore volume of the test sample at the first frame stress is calculated from:

$$\frac{P_1 \cdot V_1}{T} = \frac{P_2(V_1 + V_2 + V_p)}{T} \quad [8]$$

Where:

T = temperature

Pressures and volumes are as defined above.

After helium is vented through valve 11 and exhaust 12, frame stress is adjusted to a second selected pressure, e.g., about 3,500 psi. The pore volume at the second frame stress is then determined in the same manner as for the first frame stress.

Figure 2:
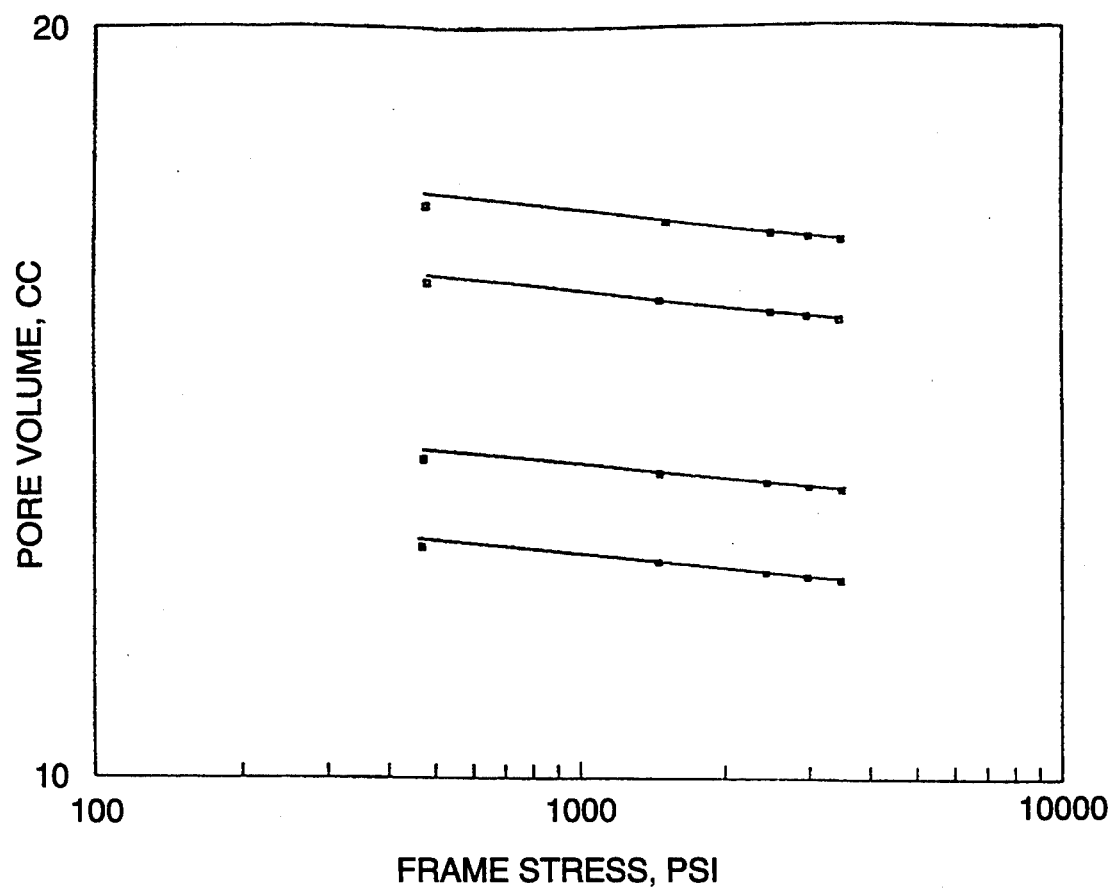
FIG. 2 is a bi-logarithmic plot of pore volume versus frame stress for carbonate rock samples.
Figure 3:
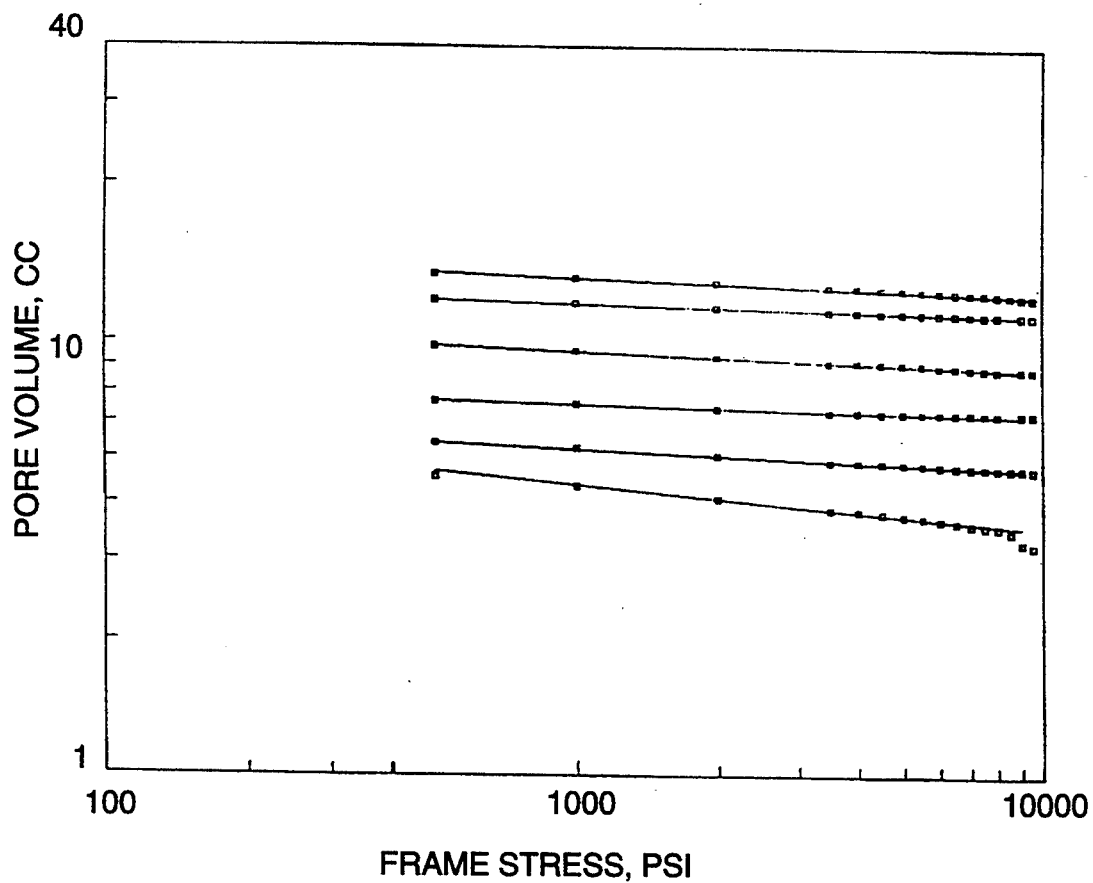
FIG. 3 is a bi-logarithmic plot of pore volume versus frame stress for sandstone rock samples.

The data for the sample are expressed in an exponential relationship by constructing bi-logarithmic plots of the measured pore volume versus the corresponding applied frame stress. As shown in FIGS. 2 and 3, these plots are based on more than two data points; however, reliable plots can be based on two data points since the plots are linear.

The minimum external pressure on the sample of from about 200 to 500 psi represents zero stress, or the ambient pressure condition. This low figure represents the pressure at which the sleeve of the core sample holder conforms to the surface of the core sample. The maximum pressure that can be applied must not exceed the matrix yield stress for the sample, since that is the point at which there is a failure of the rock structure. Typical matrix yield stress pressures can be up to about 10,000 psi for consolidated reservoir rock samples. Pore volume can be measured over a range of pressures; however, as noted above, samples are preferably tested at only two pressures of about 1,500 and 3,500 psi. The slope "m" and intercept "b" of the pore volume versus pressure plot are then determined. Compressibility of the reservoir rock sample at any overburden pressure is then determined according to equation [3]. Porosity at stress and relative porosity change of the sample are calculated according to equations [5] and [7], respectively.

FIG. 2 is a plot of pore volume versus pressure for several carbonate (limestone) samples. The samples were obtained at various depths to ensure a representative population since diverse porosity/permeabilities are expected for a given rock type. Measurements were taken at simulated net overburden pressures of 500 psi (the ambient condition pressure), 1,500, 2,500, 3000 and 3,500 psi. The validity of equation [2] is demonstrated by the high correlation coefficient ($R^2 > 99\%$) for the data.

FIG. 3 is a plot of pore volume versus pressure for several sandstone samples obtained using the method and apparatus described above.

Although the foregoing embodiments have been described with reference to graphic analyses, it is within the scope of the present invention to obtain the required parameters, i.e., slope and intercept, by processing the data in a suitably programmed general purpose computer.

We claim:

1. A method for determining pore volume compressibility of a rock sample comprising the steps of:
   (a) measuring the pore volume of the rock sample at a first pressure;
   (b) varying the external pressure on said rock sample while keeping the pore pressure constant at about atmospheric pressure to attain a second pressure;
   (c) measuring the pore volume of the rock sample at the second pressure;
   (d) defining a log pore volume versus log pressure relation from the pore volume measurements of steps a and c, which relation is linear; and
   (e) determining the pore volume compressibility of the rock sample at any pressure according to $$C_p = \frac{-m}{P}$$

where:

$C_p$ is the pore volume compressibility, m is the slope of the log pore volume versus log pressure relation, and P is the simulated overburden (external) pressure.

2. The method of claim 1 where the second pressure differs from the first pressure by from about 1000 psi to about 3000 psi.

3. The method of claim 1 where the pore volume is measured at pressures of about 1,500 psi and about 3,500 psi.

4. The method of claim 1 where the second pressure is greater than the first pressure.

5. The method of claim 1 where the pore volume is measured using a helium injection-Boyle's Law porosimeter.

6. The method of claim 1 where at least one of the steps a through e is performed by a programmed general purpose computer.

7. A method for determining the porosity of a rock sample comprising the steps of:
   (a) measuring the pore volume of the rock sample at a first pressure;
   (b) varying the external pressure on said rock sample while keeping the pore pressure constant at about atmospheric pressure to attain a second pressure;
   (c) measuring the pore volume of the rock sample at the second pressure;
   (d) determining the grain volume of the rock sample;
   (e) defining a log pore volume versus log pressure relation from the pore volume measurements of steps a and c, which relation is linear; and
   (f) determining the porosity of said rock sample at any pressure according to $$\phi_s = \frac{b \cdot P_s^{-m}}{b \cdot P_s^{-m} + V_g}$$

where:

$\phi_s$ is the porosity at stress, b is the intercept of the log pore volume versus log pressure relation, m is the slope of said log—log relation, $P_s$ is the stress pressure, and $V_g$ is the grain volume.

8. The method of claim 7 where the second pressure differs from the first pressure by from about 1000 psi to about 3000 psi.

9. The method of claim 7 where the pore volume is measured at about 1,500 psi and about 3,500 psi.

10. The method of claim 7 where the second pressure is greater than the first pressure.

11. The method of claim 7 where the pore volume is measured using a helium injection-Boyle's Law porosimeter.

12. The method of claim 7 where the grain volume of the sample is determined by the helium injection-Boyle's Law method.

13. The method of claim 7 where at least one of the steps (a) through (f) are performed by a programmed general purpose computer.

14. A method for determining the relative porosity change of a rock sample comprising the steps of:
   (a) measuring the pore volume of the rock sample at a first pressure;
   (b) varying the external pressure on said rock sample while keeping the pore pressure constant at about atmospheric pressure to attain a second pressure;
   (c) measuring the pore volume of the rock sample at the second pressure;
   (d) determining the grain volume of the sample;
   (e) defining a log pore volume versus log pressure relation from the pore volume measurements of steps a and c, which relation is linear; and
   (f) determining the relative porosity change of said rock sample at any pressure according to $$\frac{\Delta\phi}{\phi_i} = 1 - \frac{b \cdot P_s^{-m}}{b \cdot P_s^{-m} + V_g} \cdot \frac{V_g + V_p}{V_{pi}}$$

where:
   $\Delta\phi/\phi_i$ is the relative porosity change,
   $V_{pi}$ is the initial pore volume,
   $V_p$ is the pore volume, and
   m is the slope of the log pore volume versus log pressure relation,
   b is the intercept of the log pore volume versus log pressure relation,
   $P_s$ is the stress pressure, and
   $V_g$ is the grain volume.

15. The method of claim 14 where the second pressure differs from the first pressure by from about 1000 psi to about 3000 psi.

16. The method of claim 14 where the pore volume measurements are obtained at about 1,500 psi and about 3,500 psi.

17. The method of claim 14 where the second pressure is greater than the first pressure.

18. The method of claim 14 where the pore volume is measured using a helium injection-Boyle's Law porosimeter.

19. The method of claim 14 where the grain volume of the sample is measured by the helium injection-Boyle's Law method.

20. The method of claim 14 where at least one of the steps a through f is performed by a programmed general purpose computer.

21. A method for determining properties of a rock sample comprising the steps of:
   (a) adjusting external pressure on the sample to attain a first external pressure while maintaining rock sample pore pressure at about atmospheric pressure;
   (b) obtaining a known volume of inert gas, where said inert gas is at about 100 psi;
   (c) exposing rock sample pores to said known volume of inert gas;
   (d) measuring the pore pressure of the rock sample;
   (e) varying the external pressure on said rock sample to attain a second external pressure while maintaining rock sample pore pressure at about atmospheric pressure;
   (f) repeating steps b through d;
   (g) determining the pore volume at said first and second external pressure according to Boyle's law;
   (h) determining from the pore volume data of step g the slope of the log pore volume versus log pressure relation; and
   (i) determining the pore volume compressibility of the rock sample at any external pressure according to $$C_p = -\frac{m}{P}$$

where:
   $C_p$ is the pore volume compressibility,
   m is the slope of the log pore volume versus log pressure relation, and
   p is the simulated overburden (external) pressure.

22. The method of claim 21 where the inert gas is helium.

23. A method for determining properties of a rock sample comprising the steps of:
   (a) adjusting external pressure on the sample to attain a first external pressure while maintaining rock sample pore pressure at about atmospheric pressure;
   (b) obtaining a known volume of inert gas, where said inert gas is at about 100 psi;
   (c) exposing rock sample pores to said known volume of inert gas;
   (d) measuring the pore pressure of the rock sample;
   (e) varying the external pressure on said rock sample to attain a second external pressure while maintaining rock sample pore pressure at about atmospheric pressure;
   (f) repeating steps b through d;
   (g) determining the pore volume at said first and second external pressure according to Boyle's law;
   (h) determining the grain volume of the rock sample;
   (i) determining from the pore volume data of step g the slope and intercept of the log pore volume versus log pressure relation; and
   (j) determining the porosity of the rock sample at any pressure according to $$\phi_s = \frac{b \cdot P_s^{-m}}{b \cdot P_s^{-m} + V_g}$$

where:
   $\phi_s$ is the porosity at stress,
   b is the intercept of the log pore volume versus log pressure relation,
   m is the slope of said log—log relation,
   $P_s$ is the stress pressure, and
   $V_g$ is the grain volume.

24. A method for determining properties of a rock sample comprising the steps of:
   (a) adjusting external pressure on the sample to attain a first external pressure while maintaining rock sample pore pressure at about atmospheric pressure;

(b) obtaining a known volume of inert gas, where said inert gas is at about 100 psi;

(c) exposing rock sample pores to said known volume of inert gas;

(d) measuring the pore pressure of the rock sample;

(e) varying the external pressure on said rock sample to attain a second external pressure while maintaining rock sample pore pressure at about atmospheric pressure;

(f) repeating steps b through d;

(g) determining the pore volume at said first and second external pressure according to Boyle's law;

(h) determining the grain volume of the rock sample;

(i) determining from the pore volume data of step g the slope and intercept of the log pore volume versus log pressure relation; and (j) determining the relative porosity change of said rock sample according to $$\frac{\Delta\phi}{\phi_i} = 1 - \frac{b \cdot P_s^{-m}}{b \cdot P_s^{-m} + V_g} \cdot \frac{V_g + V_p}{V_{pi}}$$

where:

$\Delta\phi/\phi_i$ is the relative porosity change, $V_i$ is the initial pore volume $V_p$ is the pore volume, m is the slope of the log pore volume versus log pressure relation, b is the intercept of the log pore volume versus log pressure relation, $P_s$ is the stress pressure, and $V_g$ is the grain volume.

25. An apparatus for determining the pore volume compressibility of a rock sample comprising:

(a) a porosimeter for measuring pore volume at a first and a second external pressure, where said porosimeter is adapted to vary the external pressure on the sample to attain the second external pressure and further adapted to maintain pore pressure at less than approximately 100 psi;

(b) calculating means for determining the slope of the log pore volume versus log pressure relation from the pore volume measurements of step a; and (c) calculating means for determining the pore volume compressibility of said rock sample according to $$C_p = -\frac{m}{P}$$

where:

$C_p$ is the pore volume compressibility, m is the slope of the log pore volume versus log pressure relation, and p is the simulated overburden (external) pressure.

26. An apparatus for determining the porosity of a rock sample comprising:

(a) a porosimeter for measuring pore volume at a first and a second pressure, where said porosimeter is adapted to vary the external pressure on the sample to attain the second external pressure and further adapted to maintain pore pressure at less than approximately 100 psi;

(b) means for determining the grain volume of the rock sample;

(c) calculating means for determining the slope and intercept of the log pore volume versus log pressure relation from the pore volume measurements of step (a); and (d) calculating means for determining the porosity of said rock sample according to $$\phi_s = \frac{b \cdot P_s^{-m}}{b \cdot P_s^{-m} + V_g}$$

where:

$\phi_s$ is the porosity at stress, b is the intercept of the log pore volume versus log pressure relation, m is the slope of said log—log relation, $P_s$ is the stress pressure, and $V_g$ is the grain volume.

27. An apparatus for determining the relative porosity change of a sample comprising:

(a) a porosimeter for measuring pore volume at a first and a second pressure, where said porosimeter is adapted to vary the external pressure on the sample to attain the second external pressure and further adapted to maintain pore pressure at less than approximately 100 psi;

(b) means for determining the grain volume of the rock sample; and (c) calculating means for determining the slope and intercept of the log pore volume versus log pressure relation from the pore volume measurements of step (a); and (d) calculating means for determining the relative porosity change of said rock sample according to $$\frac{\Delta\phi}{\phi_i} = 1 - \frac{b \cdot P_s^{-m}}{b \cdot P_s^{-m} + V_g} \cdot \frac{V_g + V_p}{V_{pi}}$$

where:

$\Delta\phi/\phi_i$ is the relative porosity change, $V_{pi}$ is the initial pore volume $V_p$ is the pore volume, m is the slope of the log pore volume versus log pressure relation, b is the intercept of the log pore volume versus log pressure relation, $P_s$ is the stress pressure, and $V_g$ is the grain volume.

28. A method for defining a linear relation between pore volume of a rock sample and an external pressure on the rock sample useful for determining properties of a rock sample, comprising the steps of:

(a) measuring the pore volume of the rock sample at a first pressure;

(b) varying the external pressure on said rock sample while keeping the pore pressure constant at about atmospheric pressure to attain a second pressure;

(c) measuring the pore volume of the rock sample at the second pressure;

(d) expressing the pore volume measurements as a log—log relation as a function of external pressure; and (e) defining the mathematical condition of a linear relation to exist between the measurements when the slope of the log—log relation in step (d) is observed to form a straight line plot of constant slope.

29. The method of claim 28 further comprising determining pore volume compressibility of the rock sample by:
   (i) determining the slope of the log—log relation of step d; and
   (ii) determining the pore volume compressibility of the rock sample at any pressure according to $$C_p = -\frac{m}{P}$$

where:
   $C_p$ is the pore volume compressibility,
   m is the slope of the log—log relation, and
   P is the simulated overburden (external) pressure.

30. The method of claim 28 further comprising determining porosity of the rock sample by:
   (i) determining the grain volume of the sample;
   (ii) determining the slope and intercept of the log—log relation of step d; and
   (iii) determining the porosity of the rock sample at any pressure according to $$\phi_s = \frac{b \cdot P_s^{-m}}{b \cdot P_s^{-m} + V_g}$$

where:
   $\phi_s$ is the porosity at stress,
   b is the intercept of the log—log relation,
   m is the slope of the log—log relation,
   $P_s$ is the stress pressure, and
   $V_g$ is the grain volume.

31. The method of claim 28 further comprising determining relative porosity change of the rock sample by:
   (i) determining the grain volume of the rock sample;
   (ii) determining the slope and intercept of the log—log relation of step d; and
   (iii) determining the relative porosity change of the rock sample at any pressure according to $$\frac{\Delta\phi}{\phi_i} = 1 - \frac{b \cdot P_s^{-m}}{b \cdot P_s^{-m} + V_g} \cdot \frac{V_g + V_p}{V_{pi}}$$

where:
   $\Delta\phi/\phi_i$ is the relative porosity change,
   $V_{pi}$ is the initial pore volume,
   $V_p$ is the pore volume, and
   m is the slope of the log—log relation,
   b is the intercept of the log—log relation,
   $P_s$ is the stress pressure, and
   $V_g$ is the grain volume.

32. A method for determining pore volume compressibility of a rock sample using a set of at least three measurements comprising the steps of:
   (a) measuring the pore volume of the rock sample at at least three external pressures while maintaining pore pressure at about atmospheric pressure;
   (b) expressing the set of pore volume measurements in a log—log relation as a function of external pressure;
   (c) applying a best fit approximation to establish a linear relation model among the set of measurements expressed in the log—log relation in step (b) where the set of measurements forms a nearly linear relation: or applying a linear fit to define a linear relation among the set of measurements expressed in the log—log relation in step (b) where said measurement set forms a true linear relation;
   (d) determining the slope of the linear relation model of step (c) where the log—log relation for said set of measurements is nearly linear; or determining the slope of the linear relation of step (c) where the log—log relation for said set of measurements is linear; and
   (e) determining the pore volume compressibility of the rock sample at any pressure according to $$C_p = -\frac{m}{P}$$

where:
   $C_p$ is the pore volume compressibility,
   m is the slope of the linear relation of step (c) where the set of measurements forms a true linear relation, or is the slope of the linear relation model of step (c) where the set of measurements forms a nearly linear relation, and
   P is the simulated overburden (external) pressure.

33. A method for determining porosity of a rock sample using, a set of at least three measurements comprising the steps of:
   (a) measuring the pore volume of the rock sample at at least three external pressures while maintaining pore pressure at about atmospheric pressure;
   (b) expressing the set of pore volume measurements in a log—log relation as a function of external pressure;
   (c) applying a best fit approximation to establish a linear relation model among the set of measurements expressed in the log—log relation in step (b) where the set of measurements forms a neatly linear relation; or applying a linear fit to define a linear relation among the set of measurements expressed in the log—log relation in step (b) where said measurement set forms a true linear relation;
   (d) determining the slope and intercept of the linear relation model of step (c) where the log—log relation for said set of measurements is nearly linear; or determining the slope and intercept of the linear relation of step (c) Where the log—log relation for said set of measurements is linear;
   (e) determining the grain volume of the sample; and
   (f) determining the porosity of the rock sample at any pressure according to $$\phi_s = \frac{b \cdot P_s^{-m}}{b \cdot P_s^{-m} + V_g}$$

where:
   $\phi_s$ is the porosity at stress,
   b is the intercept of the linear relation of step (c) where the set of measurements forms a true linear relation, or is the intercept of the linear relation model of step (c) where the set of measurements forms a nearly linear relation,
   m is the slope of the linear relation of step (c) where the set of measurements forms a true linear relation, or is the slope of the linear relation model of step (c) where the set of measurements forms a nearly linear relation, $P_s$ is the stress pressure, and
$V_g$ is the grain volume.

34. A method for determining relative porosity change of a rock sample using a set of at least three measurements comprising the steps of:
   (a) measuring the pore volume of the rock sample at at least three external pressures while maintaining pore pressure at about atmospheric pressure;
   (b) expressing the set of pore volume measurements in a log—log relation as a function of external pressure;
   (c) applying a best fit approximation to establish a linear relation model among the set of measurements expressed in the log—log relation in step (b) where the set of measurements forms a nearly linear relation; or applying a linear fit to define a linear relation among the set of measurements expressed in the log—log relation in step (b) where said measurement set forms a true linear relation;
   (d) determining the slope and intercept of the linear relation model of step (c) where the log—log relation for said set of measurements is nearly linear; or determining the slope and intercept of the linear relation of step (c) where the log—log relation for said set of measurements is linear;
   (e) determining the grain volume of the sample; and
   (f) determining the relative porosity change of the rock sample at any pressure according to $$\frac{\Delta\phi}{\phi_i} = 1 - \frac{b \cdot P_s^{-m}}{b \cdot P_s^{-m} + V_g} \cdot \frac{V_g + V_p}{V_{pi}}$$

where:
   $\Delta\phi/\phi_i$ is the relative porosity change,
   $V_{pi}$ is the initial pore volume,
   $V_p$ is the pore volume, and
   b is the intercept of the linear relation of step (c) where the set of measurements forms a true linear relation, or is the intercept of the linear relation model of step (c) where the set of measurements forms a nearly linear relation,
   m is the slope of the linear relation of step (c) where the set of measurements forms a true linear relation, or is the slope of the linear relation model of step (c) where the set of measurements forms a nearly linear relation,
   $P_s$ is the stress pressure, and
   $V_g$ is the grain volume.

* * * * *

UNITED STATES PATENT AND TRADEMARK OFFICE
CERTIFICATE OF CORRECTION

PATENT NO. : 5,442,950
DATED : August 22, 1995
INVENTOR(S) : Unalmiser et al.

It is certified that error appears in the above-indentified patent and that said Letters Patent is hereby corrected as shown below:

Col. 3, line 42, change "Wherein:" to —Where:—.
Col. 4, line 44, change "Four" to —For—.

Col. 9, line 28, change "Vi" to —Vpi—.
Col. 12, line 26, delete "," after —using—.
Col. 12, line 37, change "neatly" to —nearly—.
Col. 12, line 47, change "Where" to —where—.

Signed and Sealed this

Twenty-eighth Day of November 1995

Attest:

BRUCE LEHMAN

*Attesting Officer*   *Commissioner of Patents and Trademarks*